United States Patent [19]

Itoh et al.

[11] Patent Number: 4,856,890
[45] Date of Patent: Aug. 15, 1989

[54] OPHTHALMIC PHOTOGRAPHING DEVICE

[75] Inventors: Yuji Itoh, Chigasaki; Junichi Takahashi, Kawasaki, both of Japan

[73] Assignee: Canon Kabushiki Kaisha, Tokyo, Japan

[21] Appl. No.: 6,430

[22] Filed: Jan. 22, 1987

Related U.S. Application Data

[63] Continuation of Ser. No. 884,305, Jul. 15, 1986, Pat. No. 4,679,919, Continuation of Ser. No. 589,740, Mar. 15, 1984, abandoned.

[30] Foreign Application Priority Data

Mar. 22, 1983 [JP] Japan .................................. 48095

[51] Int. Cl.$^4$ .......................... A61B 3/14; G03B 29/00
[52] U.S. Cl. .................................... 351/206; 354/62
[58] Field of Search ......................... 351/206, 207, 208; 354/62

[56] References Cited

U.S. PATENT DOCUMENTS 4,558,932 12/1985 Nunokawa .
4,679,919 7/1987 Itoh et al. .

FOREIGN PATENT DOCUMENTS 0143138 11/1981 Japan .

Primary Examiner—Rodney B. Bovernick
Attorney, Agent, or Firm—Fitzpatrick, Cella, Harper & Scinto

[57] ABSTRACT

In an opthalmic photographing apparatus, capable of photographing the fundus of an eye to be examined at a variable magnification, being provided with a ring slit in an illuminating optical path at a position substantially conjugate with the front-eye-part and being further provided with a baffle at a position substantially conjugate with the crystalline lens, the slit width of a ring slit image projected onto the eye to be examined and further the size of a baffle image are variable with a magnification change.

4 Claims, 4 Drawing Sheets

OPHTHALMIC PHOTOGRAPHING DEVICE

This is a continuation division of application Ser. No. 884,305 now U.S. Pat. No. 4,679,919 filed July 15, 1986, which is a continuation of application Ser. No. 589,740, filed Mar. 15, 1984, now abandoned.

BACKGROUND OF THE INVENTION

1. Field of the Invention

This invention relates to an ophthalmic photographing apparatus, and more particularly, to an ophthalmic photographing apparatus in which the fundus of an eye to be examined is to be photographed with the angle of view changed, reduction in quantity of photographing light during narrow angle (high magnification) photography as compared with during wide angle (low magnification) photography is compensated for and which can photograph eyes even having small pupil diameters, by narrow angle photography.

2. Description of the Prior Art

In eye-fundus cameras, it is known to provide a ring slit opening in a system for illuminating an eye to be examined at a position optically substantially conjugate with the pupil of the eye to be examined, illuminate the eye from the area around the pupil thereof through a ring slit opening image formed in the pupil of the eye, and effect photographing by taking out the reflected light from the fundus of the eye from the central area of the pupil by the use of an apertured mirror for branching off the illuminating system and the photographing system.

This prevents light reflected by the cornea of the illuminating light, from entering the photographing system. Further, in eye-fundus cameras according to the prior art, it is known to provide a circular height-intercepting plate (i.e., a baffle) at a position optically substantially conjugate with the crystalline lens of the eye in the system for illuminating the eye, and to prevent the light reflected by the crystalline lens, of the illuminating light, from entering the photographing system.

In such an eye-fundus camera having a ring slit and a baffle in the illuminating system during variable magnification photography, the sizes of the ring slit and the baffle have heretofore been constant irrespective of a magnification change and correspondingly, the sizes of the ring slit image and baffle image in the eye have also been constant.

Now, to photograph the fundus of an eye at a variable magnification, in addition to a case where a lens system provided in the photographing optical path which does not overlap the illuminating optical path, that is, a lens system provided in the photographing optical path subsequent to the apertured mirror, is varied, there is a case where an objective lens provided in the photographing optical path which overlaps the illuminating optical path is varied. An eye-fundus camera which has a ring slit and a baffle in the illuminating system and which effects variable magnification photography with the objective lens changed is known, and in such camera, during a magnification change, the ring slit has been replaced by another ring slit of a different size.

However, this camera is such that the size of the ring slit image or the like is made constant in the eye to be examined irrespective of interchange of the objective lens. That is, in the example of the prior art, it has not been practiced to change the size of the ring slit image during variable magnification photography.

Therefore, in the example of the prior art, the slit width of the ring slit image which is a window for introducing the illuminating light therethrough is fixed irrespective of a magnification change and thus, during narrow angle photography, as compared with during wide angle photography, the absolute quantity of photographing light is reduced.

There has also been a disadvantage that eyes to be examined having small pupil diameters cannot be photographed. That is, even if wide angle photography is changed over to narrow angle photography for an eye having a small pupil diameter, it is difficult, owing to the deficiency of the quantity of light, to judge the eye-fundus image and generally, the diameter of the pupil to be photographed is limited by the diameter during wide angle photography. Therefore, as compared with an ordinary narrow angle fixed photography camera. The diameter of the pupil to be photographed unavoidably becomes great during narrow angle photography and thus, eyes having small pupil diameters cannot be photographed.

Another method than the method described above, it would come to mind to increase the output of a photography flash to increase the quantity of photographing light during narrow angle photography, but in this case, it would be necessary to enlarge the capacity of the capacitor of the flash to increase the electrical energy.

SUMMARY OF THE INVENTION

It is an object of the present invention to provide an ophthalmic photographing apparatus in which the slit width of the ring slit image is changed with a magnification change to thereby compensate for reduction in quantity of photographing light during narrow angle photography as compared with the quantity of photographing light during wide angle photography.

It is also an object of the present invention to provide an ophthalmic photographing apparatus in which during narrow angle photography, as compared with during wide angle photography, the slit width of the ring slit image is enlarged to enable eyes to be examined having small pupil diameter to be photographed.

It is a further object of the present invention to provide an ophthalmic photographing apparatus in which the inside diameter of the ring slit image is changed with a magnification change without the outside diameter thereof being changed.

It is still a further object of the present invention to provide an ophthalmic photographing apparatus in which the slit width of the ring slit image and the size of the baffle image are changed with a magnification change.

It is yet still a further object of the present invention to provide an ophthalmic photographing apparatus in which during narrow angle photography, as compared with during wide angle photography, the output of the photographing flash need not be increased.

The invention will become fully apparent from the following detailed description thereof taken in conjunction with the accompanying drawings.

DESCRIPTION OF THE PREFERRED EMBODIMENTS

Figure 1:
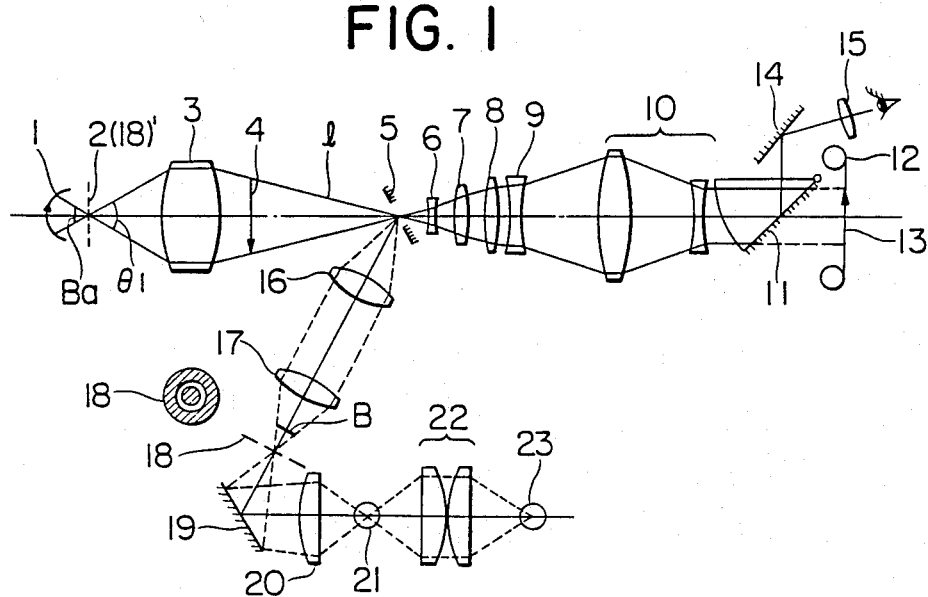
FIG. 1 shows the optical construction of a preferred embodiment of the present invention during wide angle photography.
Figure 2:
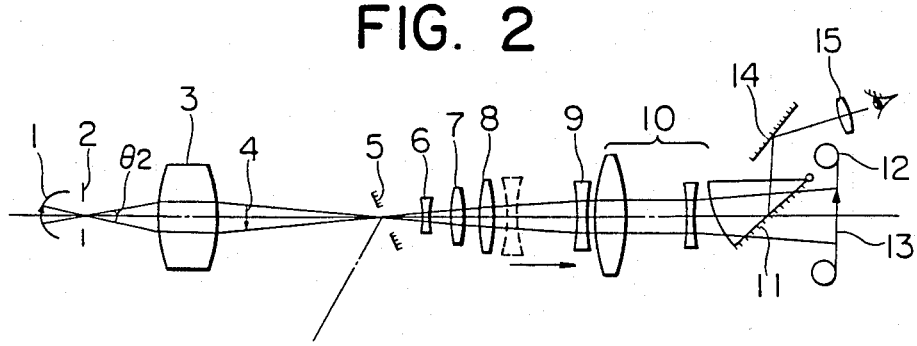
FIG. 2 shows the optical construction of only the photographing system during narrow angle photography.

FIG. 1 illustrates an illuminating system and a photographing system, and FIG. 2 illustrates a magnification changing system. Reference numerals 1 and 2 designate the fundus and pupil, respectively, of an eye to be examined. Reference numeral 3 denotes the objective lens of an eye-fundus camera, reference numeral 4 designates a primary eye-fundus image by the objective lens 3, and reference numeral 5 denotes a reflecting mirror having an opening central thereof. The centeral opening has the function of a stop, but a stop may be separately provided behind the reflecting mirror, and the stop and the pupil 2 or the cornea are conjugate with each other. Reference numeral 6 designates a movable lens group having a negative power and being movable back and forth during focusing. Reference numeral 7 denotes a stationary lens group, reference numerals 8 and 9 designate lens groups movable at one time but independently of each other during zooming, and reference numeral 10 denotes a positive relay lens group. Reference numeral 11 designates a jump-up mirror obliquely disposed during observation and retracted out of the optical path during photographing. Reference numeral 12 denotes a photographing film, and reference numeral 13 designates the final eye-fundus image which has been re-imaged by an imaging lens comprising the lenses 6 to 10. Reference numeral 14 denotes an optical path change-over mirror and reference numeral 15 designates an eyepiece. These two together constitute a finder optical system. The light ray 1 depicted by a solid line is a principal ray.

The illuminating system will now be described. The reflecting mirror 5 is obliquely disposed with respect to the optic axis of the objective lens 3 and serves to direct the illuminating light toward the objective lens 3. Reference numerals 16 and 17 designate relay lens groups, reference numeral 18 denotes a light-intercepting plate having a ring-like slit, letter B designates a baffle (a light-intercepting plate), reference numeral 19 denotes an optical path change-over mirror, reference numeral 20 designates a condenser lens, reference numeral 21 denotes a photographing light source, reference numeral 22 designates a condenser, and reference numeral 23 denotes an observation light source. The light sources 21 and 23 are conjugate with each other with respect to the condensor lens 22. The light-intercepting plate 18 and the light-source 21 are conjugate with each other with respect to the condenser lens 20. The reflecting mirror 5 and the light-intercepting plate 18 are substantially conjugate with each other with respect to the relay lens groups 16 and 17, and the reflecting mirror 5 and the pupil 2 or cornea which is the front-eye-part are conjugate with each other. The ring illuminating method using a light-intercepting plate provided with a ring-like slit, including various modifications thereof, is well known in the art and therefore need not be described.

The zoom imaging lens of the front stop will now be described in detail. First, the lens group 6 which is a lens group for focusing may be eliminated because, depending on the eye-fundus camera, it adopts a construction in which the jump-up mirror, the film and the finder are moved back and forth together to effect focusing. The stationary lens group 7 is a lens important for the correction of aberrations and the action of this lens cannot be substituted for by any other lens group. That is, this lens has the correcting functions for correcting the aberrations of the primary image and for suppressing the fluctuation of the aberrations resulting from a magnification change. The lens designer can improve the image performance aggravated by an objective lens having a simple construction, by designing the lens while being conscious of the two corrections and thus, it becomes possible to suppress the fluctuation of the aberrations when the movable lens groups have been moved. If the zoom system of this embodiment is adapted, it is preferable to adopt a stationary lens group 7 comprising two or more element lenses.

The function of correcting the aberrations of the lens group 7 in the front stop zoom system will now be described in comparison with the method of correcting the aberrations of an ordinary zoom lens. The ordinary zoom lens comprises a focusing lens, a variator, a compensator, a stop and a relay lens, and the amount of fluctuation of aberrations in each of various zoom conditions (wide angle, intermediate and telephoto) is corrected by three basic elements, i.e., the focusing lens, the variator and the compensator. That is, the absolute amount of the aberrations in each zoom condition is not reduced, but the difference in aberrations between the various conditions is reduced. Thereafter, to reduce the absolute amount of aberrations, the relay lens is used to correct the aberrations. The reason why this is possible is that the photographing stop lies between the compensator and the relay lens and also the principal ray having exited from the compensator passes through the relay lens substantially in a similar state irrespective of the various zoom conditions.

On the other hand, in the case of the present embodiment, the position through which the principal ray passes is greatly varied and thus, a stationary lens group is provided near the stop to endow the stationary lens group with an aberration correcting function approximate to that of the ordinary zoom lens. The positions of the lens group 6 and the lens group 7 can be interchanged with each other.

Reference numerals 8 and 9 designate lens groups which are movable during zooming. In order that the rearward lens group 9 having a negative power may be endowed chiefly with the function of changing the focal length and that the forward lens group 8 having a positive power may be endowed chiefly with the function of compensating for the image plane movement, the absolute value of the focal length of the lens group 8 is greater than the absolute value of the focal length of the lens group 9. It is also possible to select the power of be lens group 8 to the negative.

The relay lens group 10 is formed into a telephoto type to make the system comprising a stop and an imaging lens into a telecentric optical system, for example, on the wide angle side. Accordingly, at the wide angle end of FIG. 1, the principal ray 1 enters the imaging plane (the film surface) perpendicularly thereto.

FIG. 1 shows the optical arrangement during wide angle photography, whereas FIG. 2 shows the optical arrangement during narrow angle photography. Here, $\theta_1 > \theta_2$.

Figure 3:
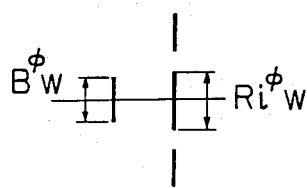
FIGS. 3 and 4 show the sizes and arrangements of the ring slit image and the baffle image during wide angle photography and during narrow angle photography, respectively.
Figure 4:
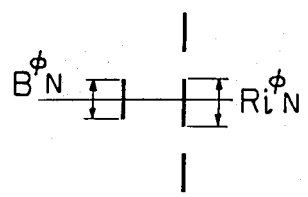

FIGS. 3 and 4 show the arrangements of the ring slit and baffle during wide angle photography and during narrow angle photography, respectively, Here, $B_W > B_N$ and $R_{iW} > R_{iN}$.

Figure 5:
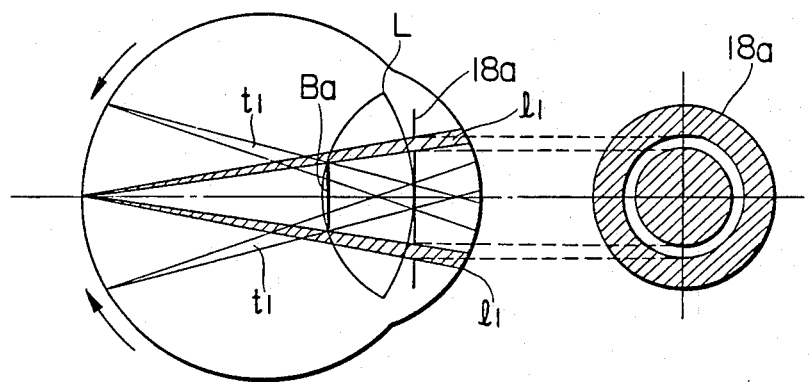
FIGS. 5 and 6 show the states of the illuminating light flux and the photographing light flux in the eyeball during wide angle photography and during narrow angle photography, respectively.
Figure 6:
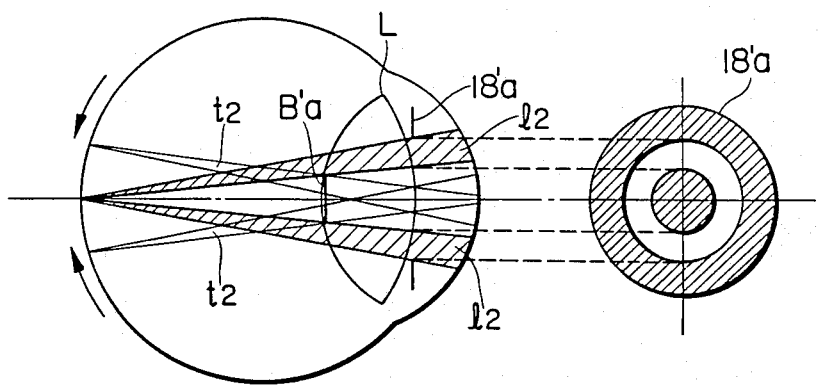

FIGS. 5 and 6 show the optical paths in the eye during wide angle photography and during narrow angle photography, respectively.

In order that illuminating light fluxes $l_1$ and $l_2$ may not intersect photographing light fluxes $t_1$ and $t_2$ on the crystalline lens L, it is necessary that the ring slit image 18a during wide angle photography have an inside diameter greater than that of the ring slit image 18a′ during narrow angle photography. Preferably, but not necessarily, the outside diameters of the ring slit images 18a and 18a′ are equal to each other. Also, it is necessary that the baffle image Ba during wide angle photography have an outside diameter greater than that of the baffle image B′a during narrow angle photography. The baffle images Ba and B′a are shielding images and not real shielding bodies, and they control the light incident on the eye fundus but have no shielding effect to the light reflected by the eye fundus and thus, the light reflected by the eye fundus may be taken out from the pupil into the photographing system through the baffle image positions Ba and B′a.

Also, the photographing side of the apertured mirror is disposed optically, substantially conjugate with the pupil, but since the diameter of the pupil is smaller than the inside diameter of the ring slit image 18′a during narrow angle photography, it is not necessary to change the diameter during a magnification change.

Figure 7:
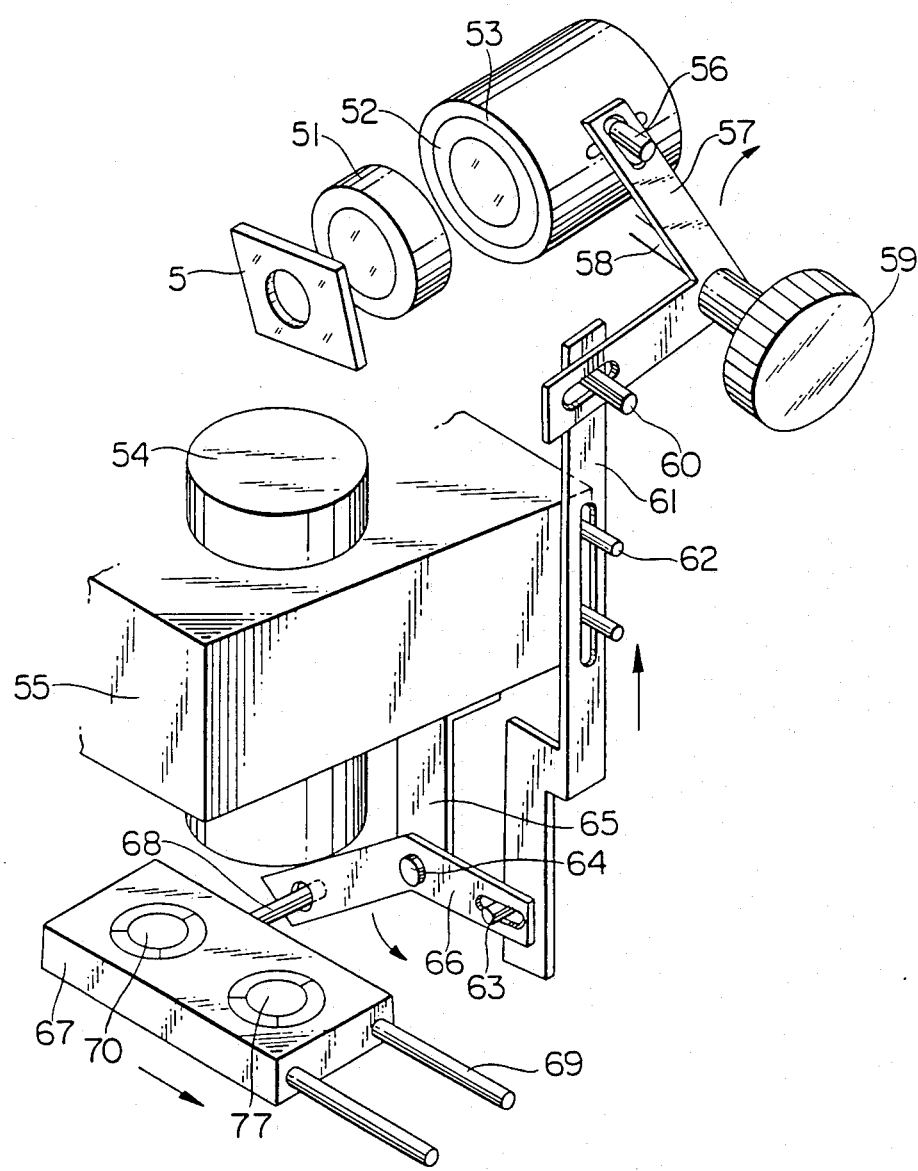
FIGS. 7 to 9 show an embodiment of the system for changing the ring slit and baffle with a magnification change.
Figure 8:
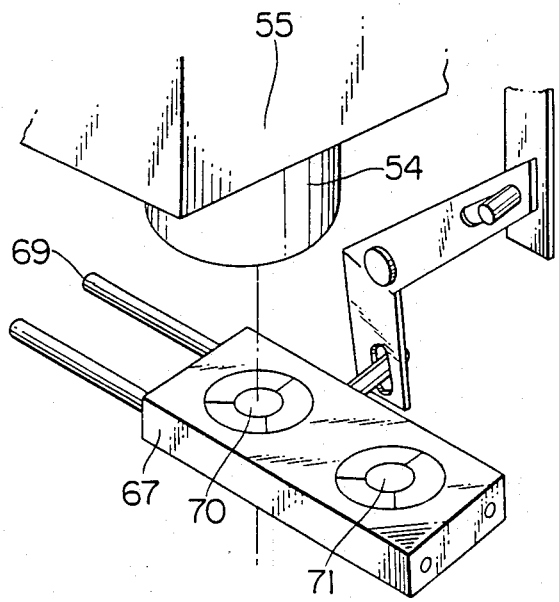
Figure 9:
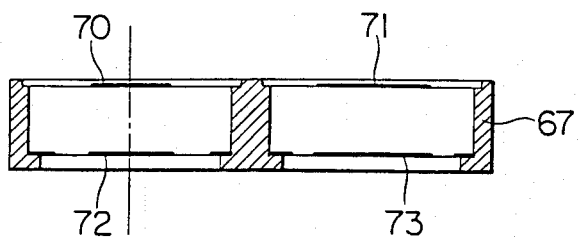

As will be apparent from the foregoing description, comparing the ring slit images 18a and 18′a, during narrow angle photography, the slit width is widened and a greater quantity of illuminating light can be directed to the eye fundus to thereby compensate for the difficulties during narrow angle (high magnification) photography in which the quantity of photographing light is usually deficient. Also, the minimum pupil diameter to be photographed during narrow angle photography can be selected to be a small value. FIGS. 7 to 9 show an embodiment of the changing system for the ring slit and baffle during a magnification change. Reference numeral 5 designates an apertured mirror, reference numeral 51 denotes a photographing lens system barrel, reference numeral 52 designates a magnification changing lens barrel, and reference numeral 53 denotes a magnification changing lens barrel support member. The magnification changing lens barrel 52 has a pin 56 fixed thereto and is slidable in a slot-like opening provided in the magnification changing lens barrel support member. Since the pin 56 is fixed to the magnification changing lens barrel 52, the magnification changing lens barrel 52 can be moved in the direction of the optic axis by sliding the pin 56. Designated by 57 is a magnification changing lever rotatable about a shaft 58. Denoted by 59 is a magnification changing knob fixed to the magnification changing lever 57. Reference numerals 60 and 63 designate pins fixed to an interlocking lever 61. The openings of the magnification changing lever 57 in which the pins 56 and 60 are received are in the form of slots. The interlocking lever 61 is adapted to slide along a guide pin 62. The guide pin 62 is fixed to the lens holder 55 of the illuminating relay lens system barrel 54.

Reference numeral 66 designates a driving lever which is rotatable about a rotary shaft 64. The rotary shaft 64 is fixed to a rotary shaft mounting plate 65. The rotary shaft mounting plate 65 is fixed to the lens holder 55. Designated by 67 is a ring slit and light-intercepting plate mounting plate which is slidable along two guide shafts 69 in a direction perpendicular to the optical axis. A pin 68 is fixed to the ring slit and light-intercepting plate mounting plate. The openings of the driving lever 66 in which the pins 63 and 68 are received are in the form of slots. Reference numerals 70 and 71 denote light-intercepting plates, and reference numerals 72 and 73 designate ring slits.

FIG. 7 shows the positions of the magnification changing lens barrel, the ring slits and the light-intercepting plates in the case of wide angle. In this state, the ring slit and light-intercepting plate for wide angle are in the illuminating optical path. When the magnification changing knob 59 is rotated clockwise so as to move the magnification changing lens toward the narrow angle side, the magnification changing lever 57 rotates and the magnification changing lens barrel 52 moves in the direction of the optical axis through the pin 56. At the same time, the interlocking lever 61 moves through the pin 60 and the driving lever 66 is rotated through the pin 63. When the driving lever 66 is rotated, the ring slit and light-intercepting plate mounting plate 67 moves along the guide shaft 69 through the pin 68 and thus, as shown in FIG. 8, the ring slit and light-intercepting plate for narrow angle come into the illuminating optical path.

FIG. 9 shows a cross-sectional view of the ring slit and light-intercepting plate mounting plate 67. Light-intercepting plates 70, 71 and ring slits 72, 73 are fixed to the ring slit and light-intercepting plate mounting plate by an adhesive agent or the like.

According to the present invention, as described above, there can be provided an opthalmic photographing apparatus in which, during narrow angle photography, as compared with during wide angle photography, reduction in quantity of photography light is compensated for and which can photograph eyes to be examined having small pupil diameters.

What we claim is:

1. An ophthalmic photographing apparatus, comprising:
   a variable magnification photographing means for photographing a fundus of an eye to be examined;
   an illuminating means to make an image of an annular aperture having an outside diameter and an inside diameter substantially at the front-eye-part of the eye to be examined for illuminating the fundus of the eye;
   means to decrease the size of the inside diameter of said image of said annular aperture at the front eye part of the eye to be examined when the magnification level of said variable magnification photographing means is increased; and
   means to increase the light-transmitting area of the image of said annular aperture at the front eye part of the eye to be examined when the magnification level of said variable magnification photographing means is increased.

2. An ophthalmic apparatus, comprising:
   a variable magnification imaging means for imaging a fundus of an eye to be examined both at a narrow angle and at a wide angle;

an illuminating means to make an image of an annular aperture having an outside diameter and an inside diameter substantially at the front-eye part of the eye to be examined for illuminating the fundus of the eye;

means to decrease the size of the inside diameter of said image of said annular aperture of the front eye part of the eye to be examined at a narrow angle imaging; and means to increase the light-transmitting area of the image of said annular aperture at the front eye part of the eye to be examined at a narrow angle imaging.

3. An ophthalmic photographing apparatus according to claim 1, further comprising a baffle provided in the illuminating optical path for illuminating the fundus of the eye at a position substantially conjugate with the crystalline lens of the eye.

4. An ophthalmic photographing apparatus according to claim 3, wherein the size of the outside diameter of the image of said baffle at the crystalline lens of the eye is decreased when the magnification level of said variable magnification photographing means is increased.

* * * * *

UNITED STATES PATENT AND TRADEMARK OFFICE
CERTIFICATE OF CORRECTION

PATENT NO. : 4,856,890
DATED : August 15, 1989
INVENTOR(S) : Yuji Itoh, et al.

It is certified that error appears in the above-identified patent and that said Letters Patent is hereby corrected as shown below: ON TITLE PAGE:

[30]   Foreign Application Priority Data

"Japan.......48095" should read --Japan.......58-48095--.

[57]   ABSTRACT:

Line 1, "opthalmic" should read --ophthalmic--.

COLUMN 1:

Line 4, "division" should be deleted.

Line 38, "tantially" should read --stantially--.

COLUMN 2:

Line 18, "camera. The" should read --camera, the--.

COLUMN 3:

Line 23, "central" should read --centrally--, and "centeral" should read --central--.

Line 59, "condensor" should read --condenser--.

UNITED STATES PATENT AND TRADEMARK OFFICE
CERTIFICATE OF CORRECTION

PATENT NO. : 4,856,890

DATED : August 15, 1989

INVENTOR(S) : Yuji Itoh, et al.

It is certified that error appears in the above-identified patent and that said Letters Patent is hereby corrected as shown below:

COLUMN 4:

Line 42, "inrespective" should read --irrespective--.

Line 62, "be" should read --the--, and "the" should read --be--.

COLUMN 5:

Line 56, "member." should read --member 53.--.

Signed and Sealed this

Seventh Day of July, 1992

Attest:

DOUGLAS B. COMER

Attesting Officer     Acting Commissioner of Patents and Trademarks